United States Patent
Zille (10) Patent No.: US 12,029,451 B2
(45) Date of Patent: Jul. 9, 2024

(54) BURR HOLE COVER INCLUDING EXTERNAL SERRATIONS

(71) Applicant: OsteoMed LLC, Addison, TX (US)

(72) Inventor: Devid R. Zille, Addison, TX (US)

(73) Assignee: OsteoMed LLC, Addison, TX (US)

( * ) Notice: Subject to any disclaimer, the term of this patent is extended or adjusted under 35 U.S.C. 154(b) by 0 days.

(21) Appl. No.: 16/869,463

(22) Filed: May 7, 2020

(65) Prior Publication Data

US 2021/0346061 A1  Nov. 11, 2021

(51) Int. Cl.
| | | |
|---|---|---|
| A61B 17/80 | (2006.01) | |
| A61B 17/68 | (2006.01) | |
| A61N 1/05 | (2006.01) | |
| A61B 17/56 | (2006.01) | |
| A61B 90/10 | (2016.01) | |

(52) U.S. Cl.
CPC ............ *A61B 17/688* (2013.01); *A61B 17/80* (2013.01); *A61B 17/808* (2013.01); *A61N 1/0534* (2013.01); *A61B 2017/568* (2013.01); *A61B 2090/103* (2016.02)

(58) Field of Classification Search
CPC .............. A61B 17/80; A61B 2090/103; A61B 2017/568; A61B 5/031; A61N 1/0534; A61N 1/0539
See application file for complete search history.

(56) References Cited

U.S. PATENT DOCUMENTS

| | | | | |
|---|---|---|---|---|
| 5,927,277 A * | 7/1999 | Baudino | ............... | A61N 1/0539 600/386 |
| 6,618,623 B1 * | 9/2003 | Pless | .................. | A61N 1/37518 607/45 |
| 7,704,260 B2 * | 4/2010 | Skakoon | ................ | A61B 90/11 606/130 |
| 8,182,540 B2 * | 5/2012 | Lin | ...................... | A61B 5/6814 607/45 |
| 8,608,650 B2 * | 12/2013 | Mangiardi | ......... | A61B 17/3439 600/184 |
| 9,572,973 B2 * | 2/2017 | Chavez | .................. | A61F 2/2875 |
| 2009/0112278 A1 * | 4/2009 | Wingeier | ............. | A61B 5/4064 607/45 |
| 2016/0193008 A1 * | 7/2016 | Gale | .................... | A61N 1/0529 604/8 |
| 2020/0069254 A1 * | 3/2020 | Lange | .................... | A61B 5/293 |

* cited by examiner

*Primary Examiner* — Tracy L Kamikawa
(74) *Attorney, Agent, or Firm* — K&L Gates LLP (57) ABSTRACT

The present disclosure provides a burr hole cover (e.g., burr hole cover) and method of manufacturing such apparatus. The burr hole cover disclosed herein may be multi-functional in that it may be used to: (a) form a burr hole which provides access to the brain, and (b) facilitate concealing the burr hole without employing any fastening devices (e.g., surgical screws, wires, etc.). In embodiments, the burr hole cover may include a sleeve having an outer surface, an inner surface, and a hollowed portion. In embodiments, the outer surface of the sleeve may define external serrations. The sleeve may be configured to create a burr hole in a skull, and the external serrations may be configured to secure the sleeve within the burr hole. The burr hole cover may also include a plate configured to fit with the sleeve and conceal the burr hole.

15 Claims, 8 Drawing Sheets

BURR HOLE COVER INCLUDING EXTERNAL SERRATIONS

TECHNICAL FIELD

The present disclosure generally relates to burr hole covers and a method of manufacturing such covers.

BACKGROUND

Craniotomy is a surgical procedure generally performed to treat neurosurgical conditions and diseases. A craniotomy may involve forming one or more burr holes—which are small holes (e.g., 8-10 mm in diameter) created in the skull through to the level of the dura—to provide a surgeon access to the brain. The access allows a surgeon to perform a desired neurosurgical procedure (e.g., deep brain stimulation). However, forming burr holes often leads to skull defects resulting in scalp depressions that are usually unacceptable to a patient from a cosmetic perspective. In some instances, the scalp depressions may aggravate over time with the wound swelling in the early stages and the soft tissues weakening in the later stages. To prevent scalp depressions and other complexities caused by them, surgeons often conceal burr holes using burr hole covers.

Numerous different designs of burr hole covers made from different materials have been employed. However, each one of them has issues. For instance, burr hole covers made of autologous bone, muscle, or fat tissue, although highly biocompatible, are linked with donor site complications, are time consuming, and are difficult to apply on burr holes. On the other hand, polymethyl methacrylate (PMMA)-based covers can be applied to burr holes, but securing them to burr holes is time consuming; PMMA-based covers may also have a thermal reaction which may be highly toxic for surrounding tissues. In contrast, mineral grafts such as hydroxyapatites (HAs) are not toxic to the surrounding tissues and have osteo-conductive properties, but they are often too brittle and reabsorb in the presence of cerebrospinal fluid (or any liquid).

Titanium-based burr hole covers have shown promise; however, they are undesirably more pliable than necessary and lack required rigidity. Further, the titanium-based burr hole covers generally require one or more surgical screws to secure the cover with the underlying skull bone. However, employing surgical screws brings about cosmetic challenges of their own. For example, the head of the surgical screws may protrude out from the scalp and appear as undesirable crests, thus creating cosmetic complexities for a patient. In addition to the cosmetic challenges, employing surgical screws may birth other complexities. For example, the screw head may erode the skull bone underlying them, which may displace the burr hole cover from its desired position.

SUMMARY

Embodiments described herein provide a burr hole cover designed to (1) conceal a burr hole in a manner that may be implemented without employing any surgical fastening devices (e.g., surgical screws), and (2) be substantially flush with the surface of a skull. In embodiments, the burr hole cover includes external serrations (e.g., threads) configured to dig in and wedge into the inner sidewalls of a burr hole, thereby fastening the burr hole cover within the burr hole. Utilizing the external serrations as securing mechanism to firmly affix the burr hole cover at a desired position may limit and can completely obviate the need to use additional surgical fastening devices, which provides for cosmetic advantages over previous covers. Further, using the inner sidewalls as securing medium—as opposed to using the surface of the skull—allows for the burr hole cover to be more easily inserted in a manner that is substantially flush with the skull.

In embodiments, the burr hole cover may include a sleeve portion and a plate portion. In embodiments, the sleeve portion may include a cylindrical body having the external serrations defined on the outer surface of the cylindrical body, and the plate portion may overlay the sleeve portion. In operation, after forming a burr hole and generally after performing desired neurosurgical procedure, a surgeon may apply torque to the sleeve portion (e.g., using a rotary drive of an insertion tool or by hand tightening) allowing the external serrations to gain traction against the inner sidewalls of the burr hole and cut grooves into the inner side walls of the burr hole, thereby securing the sleeve portion into the burr hole. In embodiments, the plate portion may be permanently fixed to the sleeve portion, while in others the plate portion could be temporarily removed from the sleeve portion. In either embodiments, the plate portion may be used to conceal the burr hole.

The present disclosure also describes a burr hole cover (BHA) surgical kit, which may be delivered to a surgical facility and brought into a surgical room thereby reducing the preparation work of employees at the surgical facility. In embodiments, the surgical kit may include one or more devices/tools that may be utilized by the surgeon during the neurosurgical procedure, including tools used to create a burr hole, tools specific to the neurosurgical procedure to be performed by the surgeon, and tools that could be used to affix a burr hole cover within a burr hole. In embodiments, the surgical kit may include a drilling tool, which may be electrical or manual, and/or one or more drill bits. In embodiments, the surgical kit may also include one or more burr hole covers; the surgical kit may also include insertion tools configured to affix the burr hole cover within a burr hole. Further, regarding tools specific to the neurosurgical procedure (e.g., inserting leads for deep brain stimulation) the surgeon wishes to perform, the kit may include one or more stimulation leads, and one or more guides configured to guide the one or more stimulation leads to their desired location within the brain.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE FIGURES

For a more complete understanding of the disclosed methods and apparatuses, reference should be made to the embodiments illustrated in greater detail in the accompanying drawings, wherein.

It should be understood that the figures are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

For the sake of illustration, this disclosure describes burr hole covers having different configurations and designs. However, it should be appreciated that the disclosure is not intended to be limited to the designs and configurations of burr hole covers disclosed herein. The disclosure should be accorded the widest scope consistent with the principles and novel features of the burr hole cover, including presence of external serrations on its body that acts as a securing mechanism to firmly affix the burr hole cover at a desired position. The description ahead is provided to enable any person skilled in the art to make or use the disclosure. Various modifications to the disclosure will be readily apparent to those skilled in the art, and the generic principles of the use and manufacturing of the burr hole cover defined herein may be applied to other variations as well.

Figure 1:
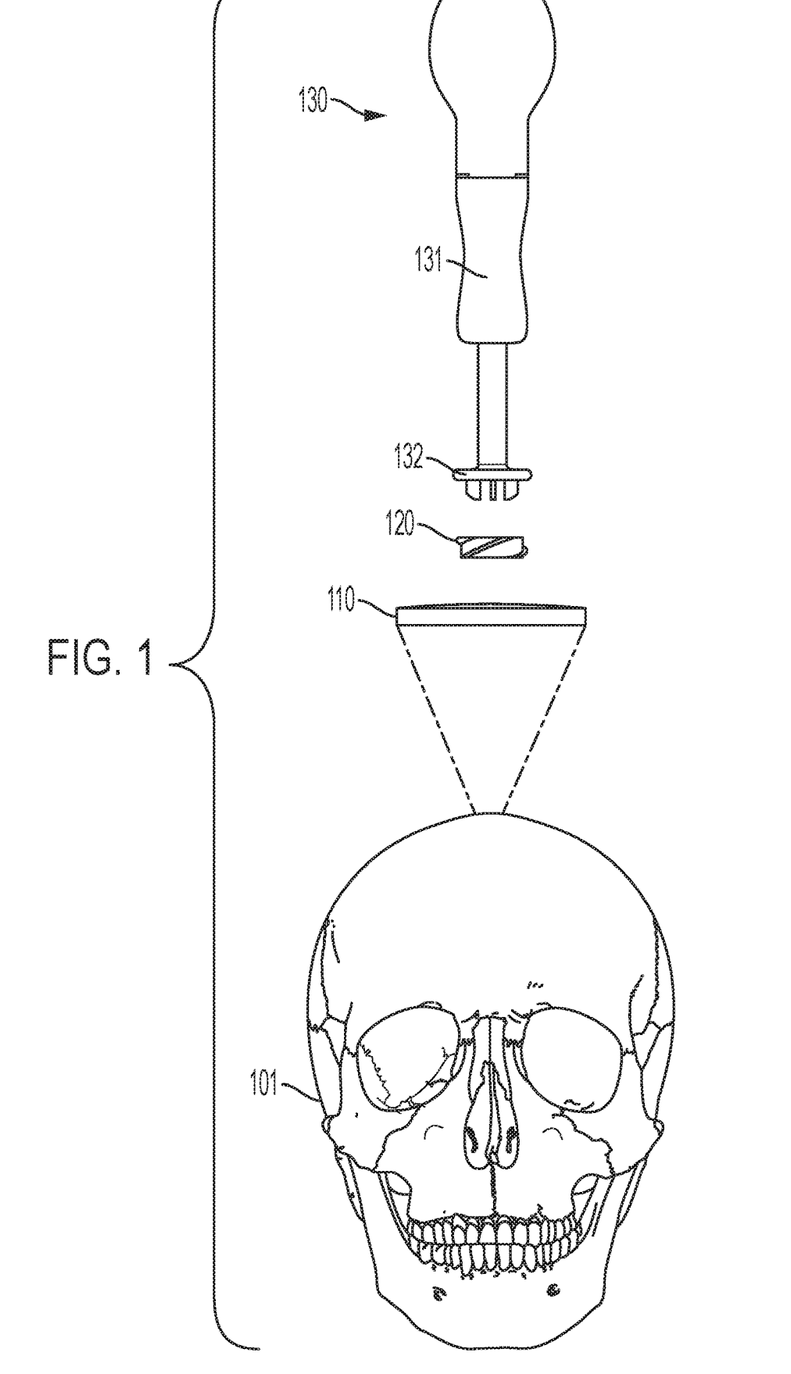
FIG. 1 depicts a perspective view of a human skull presenting one possible location at which a burr hole may be formed, in accordance with aspects of the present disclosure.

Referring to FIG. 1, a perspective view of a human skull presenting one possible location where a burr hole may be formed is shown. FIG. 1 depicts a human skull 101, a portion 110 of the human skull 101, a burr hole cover 120, and an insertion tool 130. The cross-section of the portion 110 may indicate a thickness of a human skull (e.g., 7-10 mm) through to the level of the dura. As is described in detail ahead, the burr hole cover 120 may include a sleeve, a plate, and external serrations machined along the sleeve's body. The external serrations may be designed to affix/secure the burr hole cover 120 within the burr hole, and the plate may be designed to cover the burr hole.

The disclosure ahead describes thread-like features machined along the burr hole cover; the thread-like features configured to cut grooves into the inner side walls of the burr hole so as to affix (e.g., lock and grip) the burr hole cover 120 within the burr hole. However, it should be appreciated that the disclosure is not intended to be limited to the design of external serrations disclosed herein. The disclosure should be accorded the widest scope consistent with the principles and novel features of the external serrations, including features machined along the body of the burr hole cover that are configured to mate into the inner side walls of the burr hole to form a strong and locked grip between the burr hole cover and inner sidewalls of the burr hole.

In some implementations, an insertion tool 130 may be used to provide the mechanical force needed in affixing the burr hole cover 120 within the burr hole formed in the portion 110. In some implementations, the use of insertion tool 130 may be avoided in that the burr hole cover 120 may be designed to be hand tightened into the burr hole. For example, the burr hole cover 120 may be designed to allow a user (e.g., surgeon) to provide the mechanical force needed in affixing the burr hole cover 120 within the burr hole by hand.

The insertion tool 130 may be manually or electrically driven, and may include a hand piece 131 and a driver portion 132. In embodiments, the insertion tool 130 may also be equipped with a clutch which may be configured to automatically disengage (e.g., while affixing the burr hole cover 120 within the burr hole) once the driver portion 132 touches a tissue (e.g., outer surface of the skull). This may prevent extraneous insertion of the burr hole cover 120 into the burr hole. An operator of the insertion tool 130, such as the surgeon, may hold the insertion tool 130 at the hand piece 131 and attach the burr hole cover 120 with the driver portion 132. In aspects, the driver portion 132 may be designed to fit with one or more features (e.g., ridge, depression, and the like) machined on the burr hole cover 120 (or a portion thereof). As such, in embodiments, the driver portion 132 may be provided or designed based on the configuration/design of the burr hole cover 120. For example, in an open configuration where the sleeve and plate forming the burr hole cover 120 are two different entities and can move independent of each other, the driver portion 132 may be designed to attach with the sleeve. On the other hand, in a closed configuration where the sleeve and plate are a single unit and cannot move independent of each other, the driver portion 132 may be designed to attach with the plate. Examples of driver bits designed to attach with different configurations of the burr hole cover 120 are described in detail below.

In operation, the surgeon after forming the burr hole (e.g., using appropriate burr hole drilling tool) may perform the desired neurosurgical procedure. After that, the surgeon may secure the burr hole cover 120 within the burr hole. To affix the burr hole cover 120 (or a portion thereof) within the burr hole, the surgeon may—using the insertion drill 130 having burr hole cover 120 attached thereto—place the burr hole cover 120 substantially close to the burr hole and transfer torque to the burr hole cover 120 using the rotary drive of the insertion tool 130. Due to the external serrations (e.g., threads) machined along its sleeve's body, the burr hole cover 120 may gain traction against the inner sidewalls of the burr hole, cuts grooves into the inner side walls of the burr hole, and affixes the burr hole 120 into the burr hole.

Figure 2A:
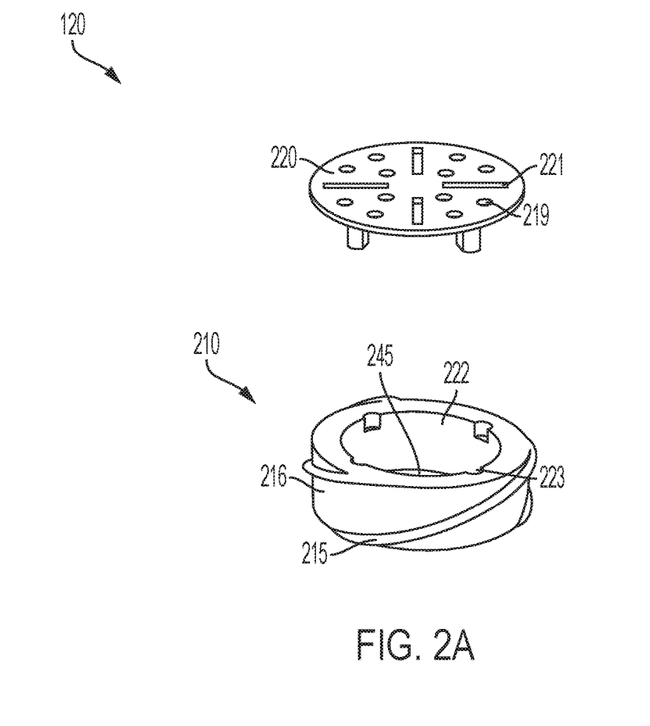
FIG. 2A depicts an illustrative burr hole cover in an open configuration, in accordance with aspects of the present disclosure.

Referring to FIG. 2A, the burr hole cover 120 in an open configuration is shown. In such configuration, the burr hole cover 120 may include a sleeve 210 and a plate 220. In aspects, the sleeve 210 and plate 220 are separate entities such that, when separated, they can move independently from each other. Because they are able to move independently, in operation, the surgeon may affix the sleeve 210 within a burr hole and attach/fit the plate 220 with the affixed sleeve 210. As such, in embodiments, the sleeve 210 includes features, such as features 223, that are designed to attach (or fit) with the plate 220 (e.g., using mating features on the plate 220). The features 223 may be present at the top side of the sleeve 210. The features 223 may facilitate transition fit or interference fit. Example of transition fit includes a tight fit where the clearance between the mating features is negligible. In a tight fit, the plate 220 can be fixed on the top side of the sleeve 210 by applying a force by hand. An example of interference fit includes press fit where the interference between the mating features may be light. In a press or a snap fit, the plate 220 can be fixed on the top side of the sleeve 210 by cold pressing. In other words, the plate 220 and the sleeve 210 are detachably connected.

In aspects, the sleeve 210 may define a cylindrical body and assume the shape of a hollow right cylinder. The sleeve 210 may include an outer surface 216, an inner surface 222, and a hollowed portion 245 The sleeve 210 may also include external serrations 215 machined/designed on the outer surface 216. In aspects, the external serrations 215 may include threads, such as ridges wrapped around the cylinder body of the sleeve 210 in the form of a helix. In aspects, the external serrations 215 may be designed to facilitate converting rotary motion into linear motion. For example, upon application of a rotary motion by a tool (e.g., insertion tool 130), the external serrations cut grooves in the inner sidewalls of the burr hole and the cylindrical body of the sleeve 210 linearly moves into the burr hole. It is noted that since the burr hole cover 120 is in open configuration, the sleeve 210 may include features that facilitate attaching the sleeve 210 to a tool (e.g., to driver portion 132 of the insertion tool 130).

Still referring to sleeve 210, it is noted above that the sleeve 210 may define a cylindrical body and assume the shape of a hollow cylinder. In aspects, the sleeve 210 may assume the shape of a right circular hollow cylinder such that both the inner and outer cylinders share the same central axis, the outer surface 216 and the inner surface 222 are substantially parallel to each other, and the diameter of the inner cylinder at the top is substantially similar to the diameter of the inner cylinder at the bottom. In embodiments, the sleeve 210 may not assume the shape of a right circular hollow cylinder. In such embodiments, at least portion of the outer surface and/or the inner surface is tapered/inclined such that the diameter of the inner cylinder at the top is different than the diameter of the inner cylinder at the bottom (e.g., the diameter at the bottom is lower than the top).

In embodiments, the sleeve 210 may be sized in view of the size (e.g., diameter) of the burr hole within which the sleeve 210 affixes itself. In embodiments, the relative diameters of the sleeve 210 and the burr hole allows the sleeve 210 to dig in and wedge into the inner sidewalls of the burr hole. Because, in principle, the external serrations are designed to wedge into the inner sidewalls of the burr hole, the diameter of the burr hole may be slightly smaller than or substantially equal to the bottom diameter of the sleeve 210. For example, if the diameter of the burr hole is 9 mm, the bottom diameter of the sleeve 210 may be substantially equal (e.g., plus/minus 10%) to 8 mm.

Yet still referring to sleeve 210, in embodiments, the sleeve 210 may be fabricated using a single type of material. For instance, the sleeve 210 may be fabricated using polyether-ether-ketone (PEEK), metal (e.g., titanium), or metal alloys (e.g., titanium alloys). In embodiments, the sleeve 210 may be fabricated using different types of materials. For instance, the cylindrical body of the sleeve (excluding the external serrations) may be fabricated using one type of material (e.g., PEEK), whereas the external serrations of the sleeve may be fabricated/machined using a second type of material (e.g., metal such as titanium). In embodiments, the sleeve 210 may have a thickness (e.g., the annular width of the sleeve 210) of about 2 mm.

Referring to the plate 220, as noted above, it is designed to fit with the sleeve 210. In aspects, the plate 220 may include features that are configured to fit with corresponding mating feature(s) machined on the sleeve 210. The fit can be transition fit or interference fit. An example of transition fit includes a tight fit where the clearance between the mating features is negligible, and an example of an interference fit includes a press fit where the interference between the mating features may be light. The plate 220 may also define apertures 219 and/or cruciform features 221 on it. These features may allow brain access or to allow for future bone growth. The plate 220 may also define apertures designed to allow surgeons to insert leads (e.g., deep brain stimulation lead) and/or drainage devices into the brain. The apertures 219 and cruciform features 221 may be optional, and thus should not be considered limiting. In embodiments, the plate 220 may be fabricated using the same material as the sleeve 220. For instance, if the sleeve 210 is fabricated using PEEK, the plate 220 may also be fabricated using PEEK. In embodiments, the plate 220 may be fabricated using a material different from the material used to fabricate the sleeve 210. For instance, if the sleeve 210 is fabricated using PEEK, the plate 220 may be fabricated using titanium or titanium alloy.

Figure 2B:
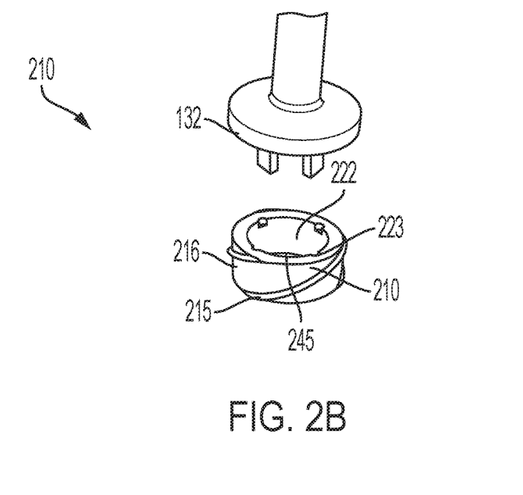
FIGS. 2B-2C depict an illustrative driver bit designed to fit with the burr hole cover of FIG. 2A, in accordance with aspects of the present disclosure.
Figure 2C:
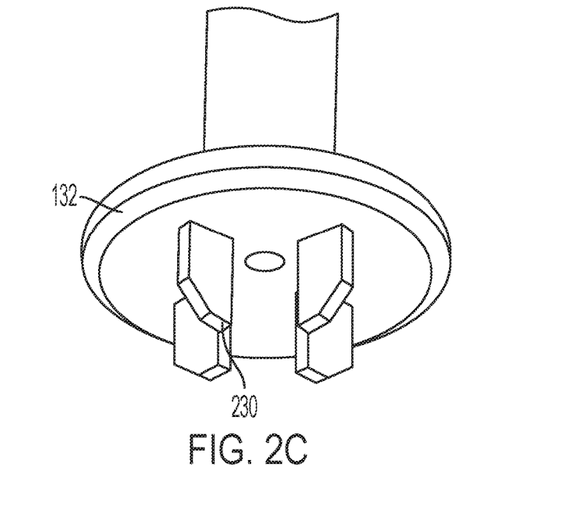

As noted above in FIG. 1, the driver portion 132 may be designed to attach/fit with the burr hole cover based 120 on its design/configuration. That said, in case of open configuration, the driver portion 132 may be designed to fit with the sleeve 210 of the burr hole cover 120. Referring to FIGS. 2B and 2C, an illustrative driver portion 132 designed to fit with the sleeve 210 (or burr hole cover 120 in an open configuration) is shown. The driver portion 132 may include features, such as features 230 that are designed to mate/affix with its corresponding features machined on the sleeve 210. In some instances, the sleeve 210 may be mated with the driver portion 132 by the surgeon performing the neurosurgical procedure. Upon mating, the surgeon may apply torque to the sleeve 210 using the rotary drive of the insertion tool 130, and the sleeve 210—due to the threads machined along its body—sturdily secure itself in the burr hole. After performing the procedure, the surgeon may use the plate 220 to conceal the hollowed portion 245 of the sleeve 210. It is noted that the plate 220, in conjunction with covering the hollowed portion 245, may also cover the burr hole.

It is noted that in open configuration, the surgeon may perform the desired neurosurgical procedure after affixing the sleeve 210 within the burr hole via hollowed portion 245. As such, in embodiments, the sleeve 210 may be sized in view of the procedure performed by a surgeon upon affixing the sleeve 210 within the burr hole. For example, the sleeve 210 (e.g., the diameter of the inner cylinder of the sleeve 210) may be sized according to leads and/or guides utilized in a deep brain stimulation procedure. In embodiments, the sleeve 210 may be designed to improve the sleeve's grip on the one or more leads. The grip may be improved by altering the freedom of movement of the leads/guides and limiting their lateral movement. In embodiments, this may be achieved by adapting the design of the sleeve 210 to include a collar which may be attached to the inner surface 222 of the sleeve 210. In embodiments, the collar may further be designed to restrict the movement of the one or more leads while the guide (used to position the one or more leads to a desired location within the brain) is being retracted. The adapted design may also help in keeping the electrodes at the distal end of the one or more leads at the target location within the brain.

Figure 3A:
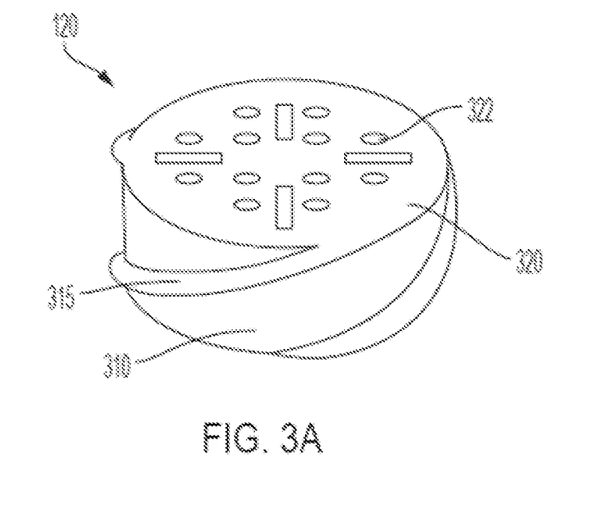
FIG. 3A depicts an illustrative burr hole cover in a closed configuration, in accordance with aspects of the present disclosure.

Referring to FIG. 3A, the burr hole cover 120 in a close configuration is shown. In this configuration, the burr hole cover 120 may still include a sleeve 310 and a plate 320, but they may be not separate entities and thus may not be able to move independently from each other. In embodiments, the sleeve 310 and plate 320 may be machined together as a single unit. In aspects, similar to the sleeve 210, the sleeve 310 may be designed to provide access to the brain and conceal the burr hole (e.g., using the plate 320 permanently affixed onto the sleeve 310). In aspects, the sleeve 310 may define a cylindrical body and assume the shape of a hollow right cylinder. The sleeve 310 may include an outer surface upon which external serrations 315 may be machined. The sleeve 310 may also include an inner surface and a hollowed portion, both of which are eclipsed by the plate 320 in FIG. 3A.

Similar to the external serrations 215, in aspects, the external serrations 315 may include threads, such as ridges wrapped around the cylinder body of the sleeve 310 in the form of a helix. In aspects, the external serrations 315 may also be designed to facilitate converting rotary motion into linear motion and affixing the burr hole cover 120 of FIG. 3A within the burr hole. The plate 320 may include features, e.g., apertures 322 that facilitate attaching the plate 320 to a tool (e.g., insertion tool 130). In aspects, the features 322, in addition for being used to attach the tool, may also relieve (e.g., decrease) pressure on the brain when fluid, such as blood, builds up and start to compress the brain. The apertures 322 may also be designed to allow surgeons to insert leads (e.g., deep brain stimulation lead) and/or drainage devices into the brain. The apertures 322 are also configured to facilitate growth of underlying biological tissue. For instance, the apertures 322 may be small perforations (e.g., 0.5 mm-1 mm in diameter) designed to allow air (or moisture) to flow towards the burr hole, which promotes skin/bone growth.

The sleeve 310, as noted above, may also define a cylindrical body and assume the shape of a hollow cylinder. In aspects, the sleeve 310 may assume the shape of a right circular hollow cylinder such that both the inner and outer cylinders share the same central axis, the outer surface and the inner surface are substantially parallel to each other, and the diameter of the inner cylinder at the top is substantially similar to the diameter of the inner cylinder at the bottom. In embodiments, the sleeve 310 may not assume the shape of a right circular hollow cylinder. In such embodiments, at least portion of the outer surface and/or the inner surface is tapered/inclined such that the diameter of the inner cylinder at the top is different than the diameter of the inner cylinder at the bottom (e.g., the diameter at the bottom is lower than the top).

Still referring to the closed configuration design of the sleeve 120 shown in FIG. 3A, the sleeve 310 and plate 320 may be fabricated using type of material. For instance, the sleeve 310 and plate 320 may be fabricated using poly-ether-ether-ketone (PEEK), metal (e.g., titanium), or metal alloys (e.g., titanium alloys). In embodiments, the sleeve 310 and plate 320 may be fabricated using different types of materials. For instance, the cylindrical body of the sleeve 310 (excluding the external serrations) and the plate 320 may be fabricated using one type of material (e.g., PEEK), whereas the external serrations 315 around the sleeve 310 may be fabricated/machined using a second type of material (e.g., metal such as titanium). In embodiments, the sleeve 310 may also have a thickness (e.g., the annular width of the sleeve 310) of about 2 mm.

Figure 3B:
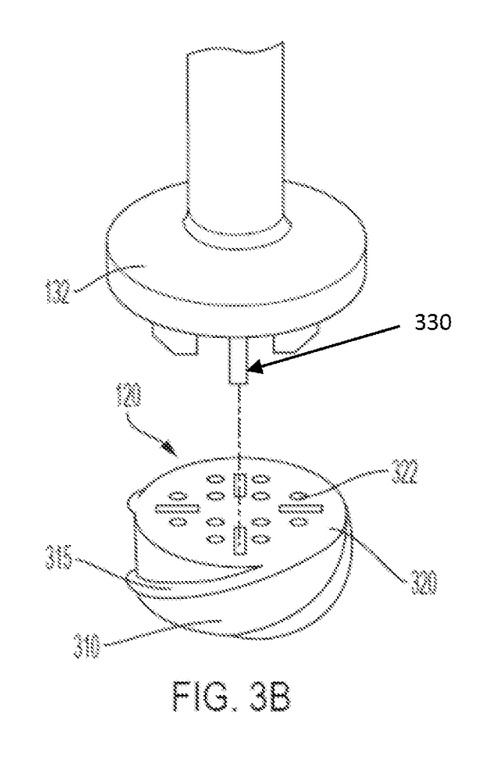
FIG. 3B depicts an illustrative driver bit designed to fit with the burr hole cover of FIG. 3A, in accordance with aspects of the present disclosure.

As noted above in FIG. 1, the driver portion 132 may be designed to attach/fit with the burr hole cover based on its design/configuration. In the case of closed configuration, the driver portion 132 may be designed to fit with the plate 320. Referring to FIG. 3B, an illustrative driver portion 132 designed to fit with the plate 320 (or burr hole 120 in a closed configuration) is shown. The driver portion 132 may include features, such as features 330 that are designed to mate/affix with its corresponding features machined on the plate 320. In some instances, the sleeve 310 may be mated with the driver portion 132 by the surgeon performing the neurosurgical procedure. Upon mating, the surgeon may apply torque to the sleeve 310 using the rotary drive of the insertion tool 130, and the burr hole cover 120 of FIG. 3A—due to the threads machined along the body of its sleeve 310—sturdily secure itself within the burr hole. The surgeon may use the burr hole cover 120 in the closed configuration to relieve pressure on brain—via the hollowed portion and features 322 of the burr hole cover 120—when fluid, such as blood, builds up and starts to compress the brain.

The burr hole cover 120 in closed configuration may be sized in view of the size (e.g., diameter) of the burr hole within which the sleeve 310 affixes itself. In embodiments, the relative diameters of the sleeve 310 and the burr hole allows the sleeve 310 to dig in and wedge into the inner sidewalls of the burr hole. Again, because, the external serrations are designed to wedge into the inner sidewalls of the burr hole, the diameter of the burr hole may be slightly smaller than or substantially equal to the bottom diameter of the sleeve 310. For example, if the diameter of the burr hole is 9 mm, the bottom diameter of the sleeve 310 may be substantially equal (e.g., plus/minus 10%) to 8 mm. The bottom diameter of the sleeve 310 may not include the diametric extension provided by the ridges created by the external serrations.

Figure 4:
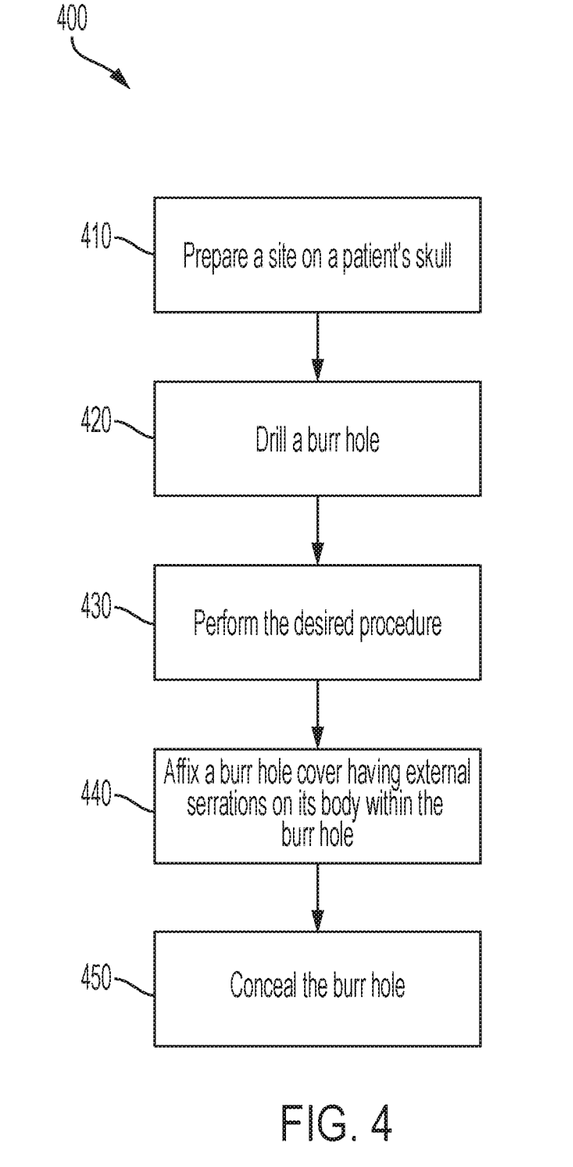
FIG. 4 depicts an illustrative method of use for the burr hole cover, in accordance with aspects of the present disclosure.
Figure 5A:
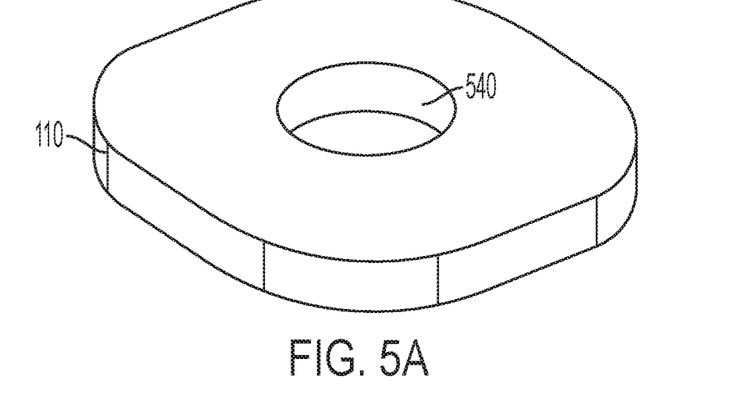
FIG. 5A-5C depict perspective views of a procedure performed using the burr hole cover of FIG. 2A; in accordance with aspects of the present disclosure.
Figure 5B:
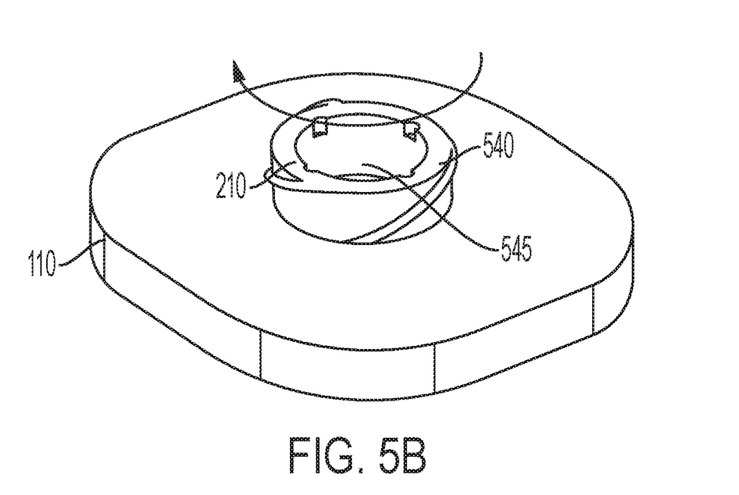
Figure 5C:
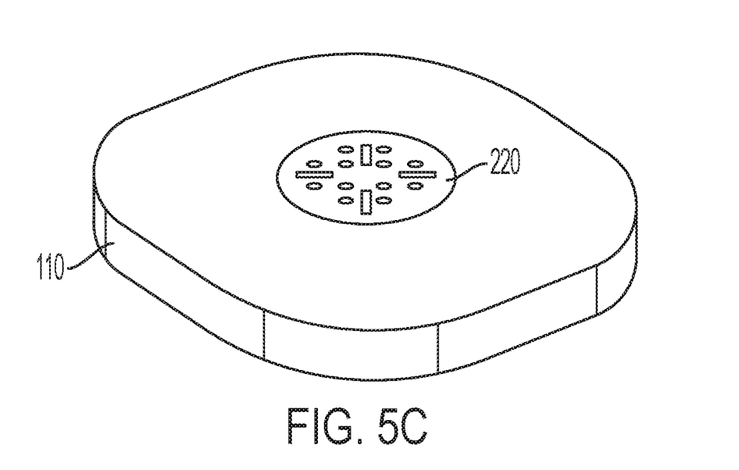

An illustrative method of use of the burr hole cover 120 is now described with respect to method 400 shown in FIG. 4. During a neurosurgical procedure, a surgeon may prepare a site on the skull of a patient by removing and/or cutting portions of the scalp covering the implant site (block 410). Once that is completed the site may be ready to be drilled. At some point after preparing the site, the surgeon may use an appropriate burr hole drilling tool to form a burr hole at the site (block 420). Following that, the surgeon may perform the desired procedure (block 430). After that the surgeon may use an insertion tool (e.g., insertion tool 130) to affix a burr hole cover within the burr hole. For example, refer to FIGS. 5A-5C, which show perspective views of a procedure that may be implemented to affix a burr hole cover in the open configuration within a burr hole formed in the portion 110. FIG. 5A depicts the portion 110 of the skull having a burr hole 540 which may be used by the surgeon to perform the procedure (e.g., as described in block 430). Following that, using an insertion tool, the surgeon may apply torque to the sleeve 210 and attach the sleeve 210 within the burr hole 540 (FIG. 5B). As noted above, the design of the sleeve 210—the external serrations digging in and wedging into the inner sidewalls of the burr hole being formed—may allow the sleeve 210 to affix within the burr hole 540. In some embodiments, instead of performing the desired procedure after forming the burr hole 540 (as described in block 430), the surgeon may perform the desired neurosurgical procedure after affixing the sleeve 210 within the burr hole 540 (that is after block 440) via the hollowed portion 545. At some point after affixing the sleeve 210 within the burr hole 540, the surgeon may fit the plate 220 with the sleeve 210 to conceal the hollowed portion 545, which in turn covers the burr hole 540 (FIG. 5C and block 450).

Figure 6A:
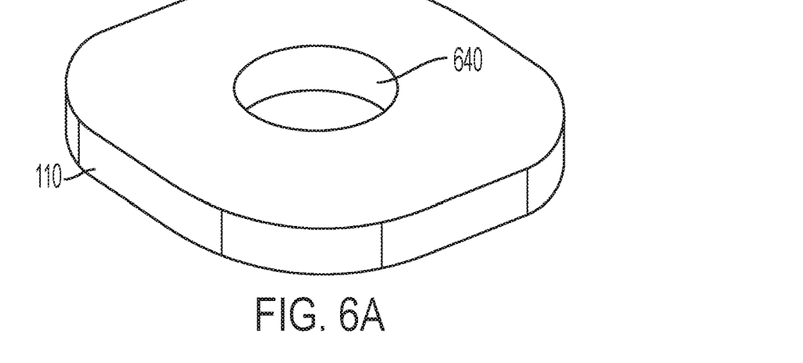
FIG. 6A-6C depict perspective views of a procedure performed using the burr hole cover of FIG. 3A; in accordance with aspects of the present disclosure.
Figure 6B:
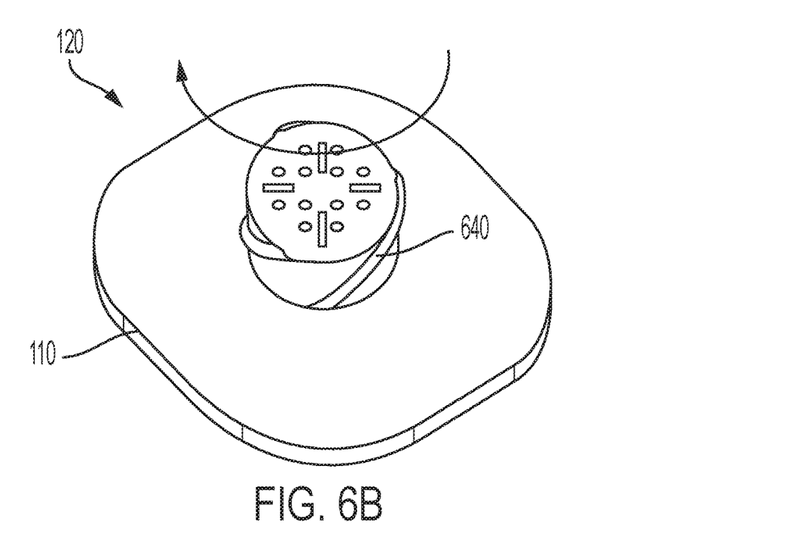
Figure 6C:
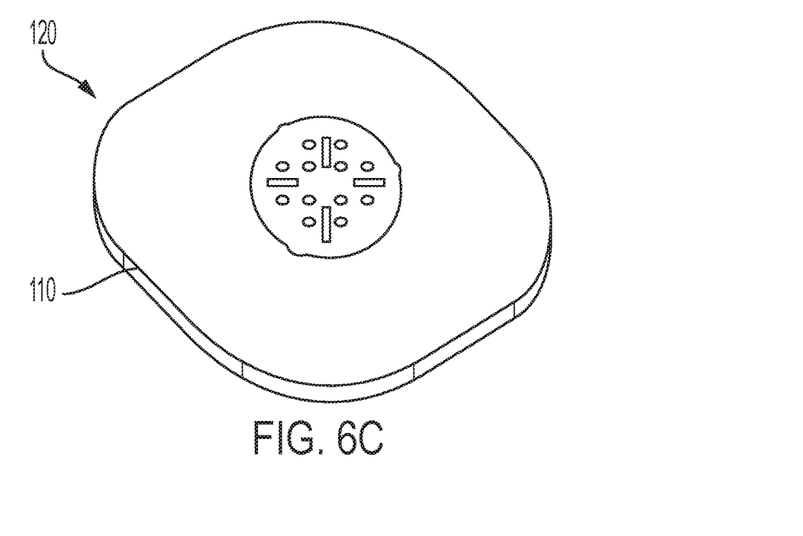

Blocks 440 and 450 of method 400 are now described with respect to the closed configuration of the burr hole cover. Referring to FIGS. 6A-6B, perspective views of a procedure performed using the burr hole cover in the closed configuration are shown. FIG. 6A depicts the portion 110 of the skull having a burr hole 640 which may be used by the surgeon to perform the procedure (e.g., as described in block 430). Following that, using an insertion tool, the surgeon may apply torque to the sleeve 310 (FIG. 6B) and affix the sleeve 310 within the burr hole 640 (FIG. 6C).

Figure 7A:
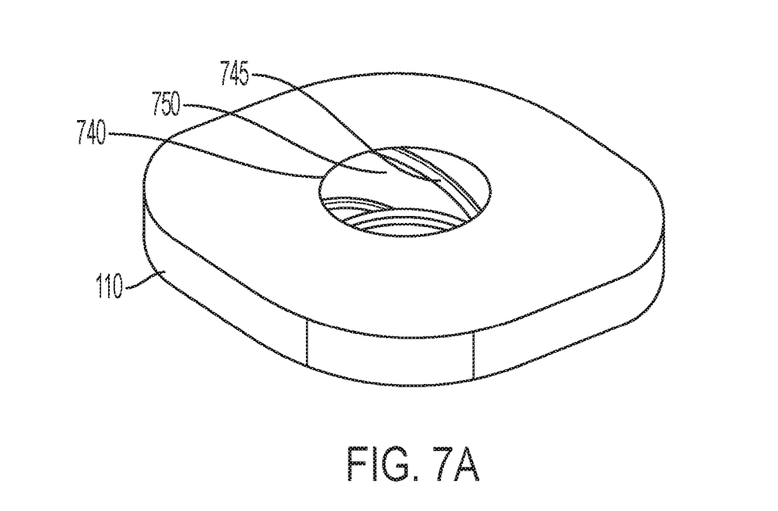
FIG. 7A depicts a perspective view of a burr hole formed using either one of the configurations of the burr hole cover, in accordance with aspects of the present disclosure.
Figure 7B:
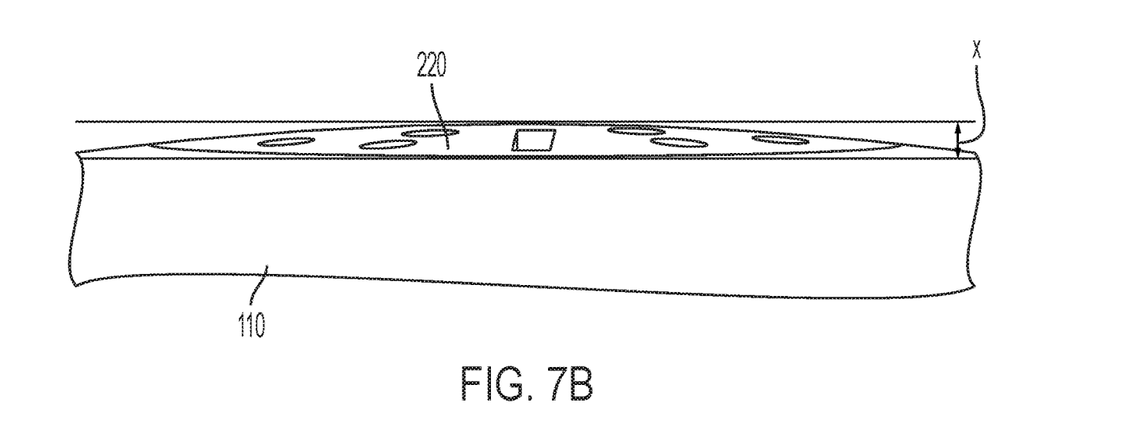
FIG. 7B depicts a cross-sectional side-view of skull affixed with burr hole cover, in accordance with aspects of the present disclosure.

Referring now to FIG. 7A, a perspective view of the portion 110 of the skull with a burr hole 740 formed using either one of the configurations of the burr hole cover 120 discussed in this disclosure is shown. FIG. 7 does not show the burr hole cover 120 affixed within the burr hole 740; it should be appreciated that FIG. 7 is disclosed to show the features (e.g., wedges/grooves) formed by the burr hole cover 120 in the inner sidewalls 750. As such, FIG. 7 depicts the inner sidewalls 750 and grooves 745 formed by the burr hole cover 120. The grooves 745 may facilitate securing the burr hole cover 120 into the burr hole 740. Referring now to FIG. 7B, a cross-sectional side-view of skull affixed with burr hole cover 120 is shown. The plate, e.g., plate 220 extends about 0.5 mm (notated as X in the figure) above the contour of the skull. This extension is substantially less than the protrusions and defects cause by the previous designs of burr hole covers.

An illustrative method for manufacture of the burr hole cover 120 is now described. In one embodiment, the burr hole cover 120 may be manufactured using additive technology, freeform fabrication, or injection molding. In embodiments, the burr hole cover 120 may be 3D printed of metal (e.g., titanium), metal alloys (e.g., titanium alloy), PEEK. In some embodiments, the burr hole cover 120 may be formed through successive fusion of chosen parts of powder layers applied to a worktable. The burr hole cover 120 formed using metal, PEEK, and similar materials have high tensile strength, impact strength, and are able to cut through bone without fracture. In alternative embodiments, other types of material that can cut through bone may be used. In some embodiments, burr hole cover 120 may be patient-specific. Patient-specific burr hole cover 120 may be individually designed for patients such that the information related to the size of the burr hole and thickness of the patient's skull where burr hole cover 120 may be secured is provided to a manufacturer before the surgery.

To illustrate, the plate 220, as shown above in open configuration, may be designed to follow the contour of the patient's skull. In embodiments, the plate 220 may be patient specific in that the plate 220 may be individually custom designed for every patient according to the contour of the patient's skull. The custom design of the burr hole cover may be created using various medical imaging techniques (e.g., CT scans, MM scans, and the like). In embodiments, both the sleeve 210 and the plate 220 are custom designed for a patient. In some embodiments burr hole cover 120 may not be patient-specific. For example, some procedures may not patient-specific apparatuses, meaning that the burr hole cover 120 is not designed for a specific patient, but is designed based on body types, gender, other generic characteristics of humans.

Figure 8:
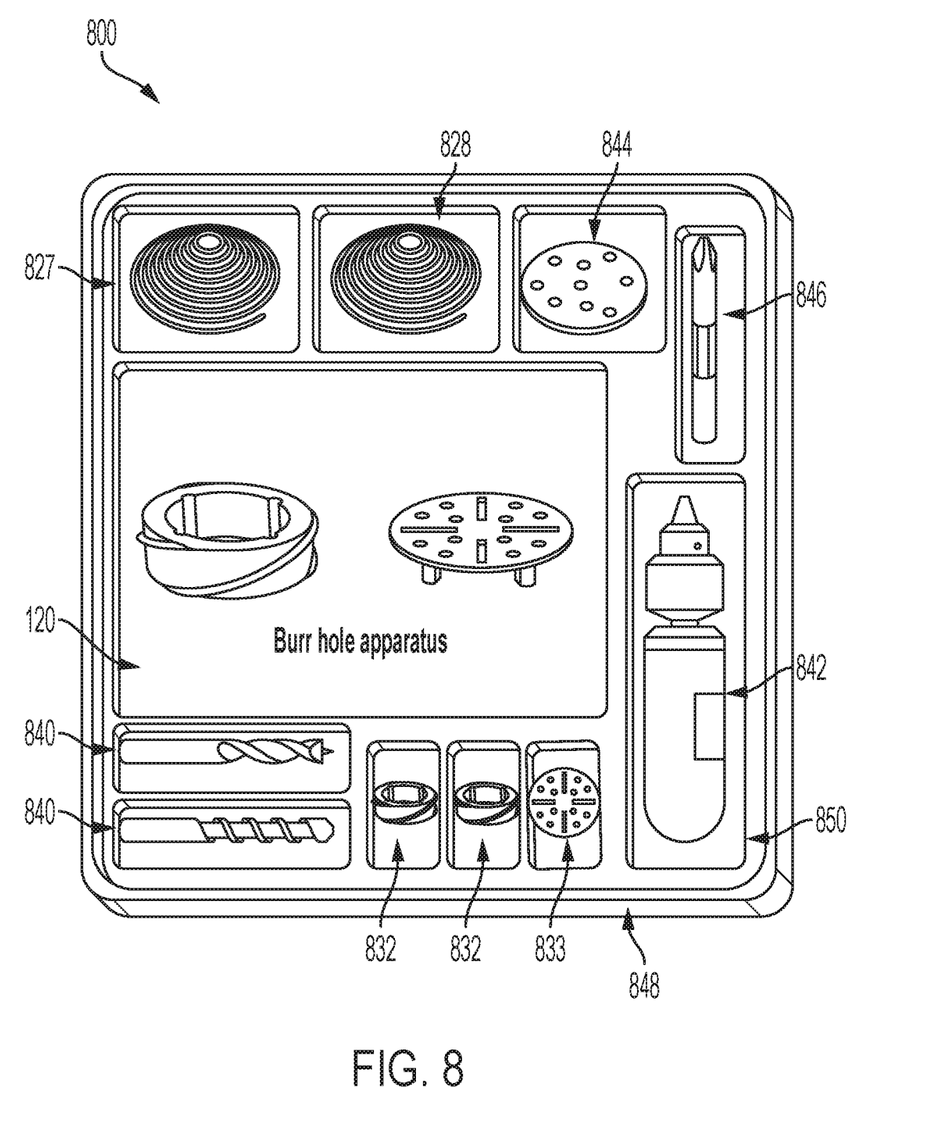
FIG. 8 depicts an illustrative burr hole cover (BHA) surgical kit, in accordance with aspects of the present disclosure.

FIG. 8 is an example illustration of a burr hole cover (BHA) surgical kit 800. BHA surgical kit 800 may be manufactured, sterilized, and packaged at a manufacturing facility. Thereafter, the sterilized package may be delivered to a surgical facility and brought into a surgical room thereby reducing the preparation work of employees at the surgical facility. Further, prepackaging at the manufacturing plant reduces the likelihood of contamination of any individual components of the kit at least because fewer people handle the components at fewer facilities. Further still, prepacking the surgical kit may save the surgical facility money and time because equipment sterilizing devices and procedures may be avoided. Yet further, because the surgical kit comes prepackaged with the components used during the procedure, the surgical kit reduces the likelihood of an employee of the surgical facility forgetting to include one or more components on a surgical tray, which results in more efficient surgeries.

Example BHA surgical kit 800 includes one or more stimulation leads 827 and/or one or more guides 828 configured to guide the one or more stimulation leads 827 to their desired location within the brain. The stimulation leads 827 may be of various thickness, length, impedance, coating material, electrode number, electrical conduit, texture, and/or other characteristics. Further, two or more stimulation leads 827 may have the same characteristics. Any number of stimulation leads 827 may be included in the BHA surgical kit 800.

BHA surgical kit 800 may also include one or more burr hole covers 120. In embodiments, the BHA surgical kit 800 may also include extra burr hole cover 120 in the surgical kit 800. The extra burr hole cover 120 are notated with numerals 832 and 833 in FIG. 8. One of the one or more burr hole covers 120 may be patient-specific and another one of the one or more burr hole covers 120 may be generic. In embodiments, the BHA surgical kit 800 may also include tools that may be used during the neurosurgical procedure. Example surgical kit 800 includes drilling tool 842, which may be electrical or manual, and/or one or more drill bits 840. The drill bits may be of the same or varying sizes. In embodiments, the one or more burr hole cover 120 may be sized to correspond to thicknesses of stimulation leads 827 and/or one or more guides 828 included in the kit. The surgical kit 800 may also include an insertion tool (e.g., insertion tool 130) configured to attach with the burr hole cover and facilitate affixing them within a burr hole.

BHA surgical kit 800 may also include one or more driving portions 846, which can attach with a burr hole cover. The surgical kit 800 may also include one or more sizing and guide instruments. The surgical kit 800 shows an example sizing wheel 844, which may be used a stencil while drilling burr holes in skull. Any number and/or type of sizing instruments may be included which may assist a surgeon with cuts, holes, placement, etc. during the procedure.

In embodiments, some or all components of the kit are embedded in a well formed in tray 848. A well helps hold a component in place on the tray while the procedure is being performed. The tray 848 may be covered by cover 850, which may be transparent, translucent, and/or opaque. A transparent cover 850 may be helpful to see the components included within the kit. During assembly of surgical kit 800, each component included in a respective kit 800 may be sterilized. Then, tray 848 and the components held thereon are sealed with sterilized cover 850. Tray 848 and cover 850 create a sterile environment therein. As a result, sealed BHA surgical kit 800 may be transported and will maintain its sterility.

In embodiments, cover 848 may be sealed such that each individual component and/or some individual components are held in separate environments. For example, cover 850 may be a plastic cover that is sealed around each well. As such, a surgeon can unseal one well without unsealing another well. Thus, if a surgeon uses one stimulation lead 827, any unused stimulation leads 827 will remained sealed in their sterile environment and may be used at a later time. It should be noted that BHA surgical kit 800 may be packaged at any facility, including a surgical facility, if desired.

While this specification contains many implementation details, these should not be construed as limitations on the scope of the invention or of what may be claimed, but rather as descriptions of features specific to particular implementations of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking may be advantageous.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A burr hole cover surgical kit comprising a burr hole cover and an insertion tool,
the burr hole cover comprising:
a sleeve having an inner surface, an outer surface, and forming an interior hollowed portion, the outer surface including one or more external serrations, wherein the external serrations are configured to secure the sleeve within a burr hole formed through to a level of dura such that the interior hollowed portion is configured to be within the burr hole; and
a plate configured to form a top surface of the burr hole cover and conceal the burr hole, wherein the plate is configured to define a plurality of apertures,
wherein the inner surface of the sleeve includes four grooves configured to mate with (i) one or more features of the plate and (ii) one or more features of the insertion tool,
wherein the plurality of apertures of the plate comprise four slits that are in a cruciform shape, and
wherein the one or more features of the insertion tool comprise four protrusions designed to fit with the four slits of the plate and the four grooves of the inner surface of the sleeve.

2. The burr hole cover surgical kit of claim 1, wherein the sleeve is further configured to allow access to a brain via the interior hollowed portion.

3. The burr hole cover surgical kit of claim 1, wherein one of the plurality of apertures is configured to facilitate growth of underlying biological tissue.

4. The burr hole cover surgical kit of claim 1, wherein one of the plurality of apertures is configured to provide access to a brain.

5. The burr hole cover surgical kit of claim 1, wherein the plate and the sleeve are detachably connected.

6. The burr hole cover surgical kit of claim 1, wherein the external serrations include ridges wrapped around the sleeve in the form of a helix.

7. The burr hole cover surgical kit of claim 1, wherein the plate is custom designed for a patient.

8. A burr hole cover surgical kit comprising a burr hole cover and an insertion tool,
the burr hole cover comprising:
a sleeve assuming a hollowed cylindrical shape, the sleeve having an inner surface, an outer surface, and a hollowed portion, wherein the outer surface includes one or more external serrations configured to secure the sleeve within a burr hole formed in a skull; and
a plate configured to form a top surface of the burr hole cover and conceal the burr hole,
wherein the plate is configured to define a plurality of apertures, wherein the plurality of apertures are configured to mate with one or more features of the insertion tool and configured to relieve a pressure on a brain, wherein the insertion tool is configured to secure the sleeve into the burr hole,
wherein the inner surface of the sleeve includes four grooves configured to mate with (i) one or more features of the plate and (ii) the one or more features of the insertion tool,
wherein the plurality of apertures of the plate comprise four slits that are in a cruciform shape, and
wherein the one or more features of the insertion tool comprise four protrusions designed to fit with the four slits of the plate and the four grooves of the inner surface of the sleeve.

9. The burr hole cover surgical kit of claim 8, wherein the hollowed portion is configured to be within the burr hole.

10. The burr hole cover surgical kit of claim 8, wherein the sleeve and the plate include titanium.

11. The burr hole cover surgical kit of claim 8, wherein the external serrations include ridges wrapped around the sleeve in the form of a helix.

12. The burr hole cover surgical kit of claim 8, wherein one of the plurality of apertures is configured to facilitate growth of underlying biological tissue.

13. The burr hole cover surgical kit of claim 8, wherein one of the plurality of apertures is configured to provide access to the brain.

14. A burr hole cover surgical kit comprising:
one or more sterile stimulation leads;
an insertion tool;
one or more sterile burr hole covers, at least one of the one or more burr hole covers comprising:
a sleeve having an inner surface, an outer surface, and forming an interior hollowed portion, the outer surface including one or more external serrations, wherein the external serrations are configured to secure the sleeve within a burr hole formed through to a level of dura such that the interior hollowed portion is configured to be within the burr hole; and
a plate configured to form a top surface of the burr hole cover and conceal the burr hole, wherein the plate is configured to define a plurality of apertures,
wherein the inner surface of the sleeve includes four grooves configured to mate with (i) one or more features of the plate and (ii) one or more features of the insertion tool,
wherein the plurality of apertures of the plate comprise four slits that are in a cruciform shape, and
wherein the one or more features of the insertion tool comprise four protrusions designed to fit with the four slits of the plate and the four grooves of the inner surface of the sleeve.

15. The burr hole cover surgical kit of claim 14, wherein the sleeve is further configured to allow access to a brain via the interior hollowed portion.

\* \* \* \* \*